United States Patent
Igney et al.

(10) Patent No.: US 9,173,613 B2
(45) Date of Patent: Nov. 3, 2015

(54) METHOD OF AUTONOMOUSLY MONITORING THE MOVEMENT ACTIVITY OF A FETUS

(75) Inventors: Claudia Hannelore Igney, Aachen (DE); Andreas Brauers, Aachen (DE); Sandrine Magali Laure Devot, Aachen (DE)

(73) Assignee: Koninklijke Philips N.V., Eindhoven (NL)

( * ) Notice: Subject to any disclaimer, the term of this patent is extended or adjusted under 35 U.S.C. 154(b) by 1207 days.

(21) Appl. No.: 12/599,067

(22) PCT Filed: May 7, 2008

(86) PCT No.: PCT/IB2008/051782
§ 371 (c)(1),
(2), (4) Date: Nov. 6, 2009

(87) PCT Pub. No.: WO2008/139372
PCT Pub. Date: Nov. 20, 2008

(65) Prior Publication Data
US 2010/0305481 A1 Dec. 2, 2010

(30) Foreign Application Priority Data
May 9, 2007 (EP) .................................. 07107853

(51) Int. Cl.
*A61B 5/00* (2006.01)
*A61B 5/11* (2006.01)
*A61B 5/0245* (2006.01)

(52) U.S. Cl.
CPC .................. *A61B 5/6892* (2013.01); *A61B 5/11* (2013.01); *A61B 5/4362* (2013.01); *A61B 5/0245* (2013.01); *A61B 5/1102* (2013.01); *A61B 5/7264* (2013.01); *A61B 2503/02* (2013.01)

(58) Field of Classification Search
CPC ...... A61B 5/11; A61B 5/1114; A61B 5/1116; A61B 5/1123; A61B 8/02; A61B 5/1102; A61B 5/4362; A61B 5/6892; A61B 5/7264
USPC .................................................. 600/587, 595
See application file for complete search history.

(56) References Cited

U.S. PATENT DOCUMENTS 4,898,179 A * 2/1990 Sirota ........................... 600/483
5,817,035 A 10/1998 Sullivan
(Continued)

FOREIGN PATENT DOCUMENTS

WO 2006111889 A1 10/2006

OTHER PUBLICATIONS

Kribeche, A., et al.; Separating fetal Doppler signals in pregnancy using Independent Component Analysis: application to the extraction of fetal heart rate and global movement; 2005; IEEE Trans. on Ultrasonics Symposium; pp. 1319-1322.

*Primary Examiner* — Max Hindenburg

(57) ABSTRACT

The present invention relates to a system (1) and method for automatically monitoring the movement activity of a fetus. In order to provide a simple and reliable technique for monitoring the movement activity of a fetus, a method of automatically monitoring the movement activity of a fetus is suggested, the method comprising the steps of: detecting (200) the overall movements of a pregnant female, said overall movements comprising movements of the pregnant female and movements of the fetus; detecting at least one second physiological signal (26) of the pregnant female; and—determining (300) the movement activity of the fetus by analyzing the detected overall movements of the pregnant female, analyzing the at least one second physiological signal (26) of the pregnant female, and discriminating movements of the pregnant female from movements of the fetus depending on the analyzing results.

8 Claims, 9 Drawing Sheets

(56) References Cited

U.S. PATENT DOCUMENTS

Figure 1:
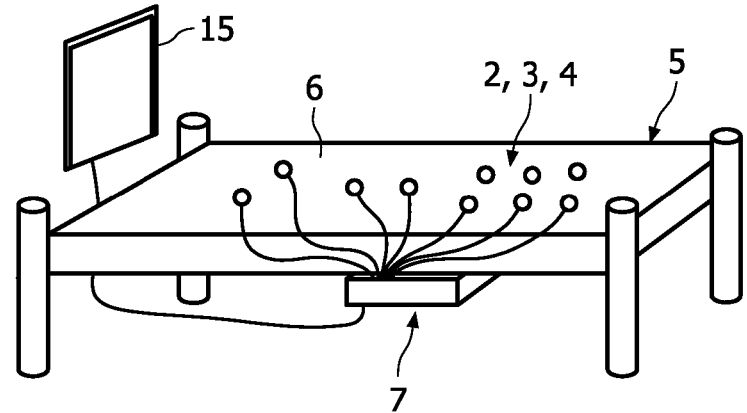

| | | |
|---|---|---|
| 6,821,258 B2 | 11/2004 | Reed et al. |
| 6,942,621 B2 * | 9/2005 | Avinash et al. ............... 600/481 |
| 7,474,915 B2 * | 1/2009 | Assaleh et al. ............... 600/511 |
| 7,680,531 B2 * | 3/2010 | Graupe et al. ............... 600/511 |
| 2004/0010210 A1 | 1/2004 | Avinash et al. |
| 2006/0229518 A1 * | 10/2006 | Ofek ............................ 600/500 |
| 2006/0241510 A1 | 10/2006 | Halperin et al. |

* cited by examiner

METHOD OF AUTONOMOUSLY MONITORING THE MOVEMENT ACTIVITY OF A FETUS

The present invention relates to a system and method for automatically monitoring the movement activity of a fetus.

A fetus is a developing mammal or other viviparous vertebrate, after the embryonic stage and before birth. In humans, the fetal stage of development begins at the end of the eighth week after fertilisation, when the major structures and organ systems have formed, until birth. Hereinafter the terms "fetus" and "unborn child" are used synonymously. Furthermore the terms "pregnant female", "pregnant woman", and "mother" are used synonymously. However, the present invention cannot only be applied to humans, but also to animals, e.g. farm animals, like horses, or pets, like dogs.

During pregnancy parents are often worried about the health of their unborn child. For example, a lack of child movements or rare child movements may be a symptom of a problematic pregnancy. For monitoring the movement activity of the unborn child, pregnant women are usually asked to count the movements of their unborn child. This is not very comfortable and prone to error.

It is an object of the present invention to provide a simple and reliable technique for monitoring the movement activity of a fetus.

This object is achieved according to the invention by a method of automatically monitoring the movement activity of a fetus, the method comprising the steps of:

detecting the overall movements of a pregnant female, said overall movements comprising movements of the pregnant female and movements of the fetus;

detecting at least one second physiological signal of the pregnant female; and determining the movement activity of the fetus by analyzing the detected overall movements of the pregnant female, analyzing the at least one second physiological signal of the pregnant female, and discriminating movements of the pregnant female from movements of the fetus depending on the analyzing results.

The object of the present invention is also achieved by a system for automatically monitoring the movement activity of a fetus, the system comprising at least one sensor for detecting the overall movements of a pregnant female, said overall movements comprising movements of the pregnant female and movements of the fetus;

at least one sensor for detecting at least one second physiological signal of the pregnant female; and an analyzing device for determining the movement activity of the fetus by analyzing the detected overall movements of the pregnant female and analyzing the at least one second physiological signal of the pregnant female; said analyzing device comprising a discriminator for discriminating movements of the pregnant female from movements of the fetus depending on the analyzing results.

The object of the present invention is also achieved by a computer program to be executed in a computer, for automatically monitoring the movement activity of a fetus, said computer program comprising computer instructions to determine the movement activity of a fetus by analyzing previously detected overall movements of a pregnant female, said overall movements comprising movements of the pregnant female and movements of the fetus;

analyzing at least one previously detected second physiological signal of the pregnant female; and discriminating movements of the pregnant female from movements of the fetus depending on the analyzing results;

when the computer program is executed in the computer.

A core idea of the invention is to use movement data of the pregnant woman, which in most cases are easy to obtain, in order to determine information about the movement activity of the unborn child. By this means an easy and completely unobtrusive way of monitoring the movement activity of an unborn child can be provided. With the present invention the evaluation and monitoring of child movements can be carried out completely automatically in a home environment.

According to the invention the determining step comprises discriminating movements of the pregnant female from movements of the fetus. In other words, the cumulative "overall" movements of the pregnant female as detected by a movement sensor are analyzed by a determining device and two different types of movement are differentiated. The first type of movement is caused by the fetus, e.g. by turning of the fetus in the uterus of the pregnant female. The second type of movement is caused by the pregnant female itself.

For discriminating those movements, at least one second physiological signal of the pregnant female is detected and analyzed. In other words, a further parameter is used for evaluating the movement data. If the second physiological signal is detected by the same detecting means (e.g. sensors) as the first physiological signal, the system costs can be reduced.

These and other aspects of the invention will be further elaborated on the basis of the following embodiments which are defined in the dependent claims.

According to a preferred embodiment of the invention, for discriminating those movements, the energy of a movement signal of the pregnant female is analyzed. More particularly, if the energy of the detected movement signal exceeds a certain threshold value, this particular movement will be assigned to a movement of the mother. If, on the other hand, the energy of the detected movement signal does not exceed a certain threshold value, this particular movement will be treated as related to a possible child movement.

According to a preferred embodiment of the invention, the second physiological signal is the pregnant female's heart rate and/or heart rate variability. According to this embodiment, a correlation between movement and heart rate of the mother is used. In cases, where a detected movement correlates with a changing heart rate of the mother, this movement is likely to be caused by the mother itself. However, in cases, where a detected movement does not correlate with a heart rate changing of the mother, this movement is likely to be caused by the fetus.

Since pregnant females usually spend a significant time in bed for resting and sleeping, the bed is an ideal place for such a monitoring task. Accordingly, in the monitoring system of the present invention the at least one sensor for detecting movements is preferably connected to or integrated into a bed. In other words, a bed is preferably used as medium for carrying out the present invention. A bed according to the present invention is defined as a surface or any other device to rest on or to sit on etc., e.g. a conventional bed, a hospital bed, a couch, a conventional chair, a dentist's chair, a wheelchair, an (operating) table, etc. However, the present invention is preferably applicable in a home environment. Accordingly, the bed is preferably a conventional bed.

All appliances described herein are adapted to carry out the method according to the present invention. All devices are constructed and programmed in a way that the procedures for obtaining data and for data processing run in accordance with the method of the invention. In particular, the analyzing device for determining the movement activity is constructed and programmed in a way that movements of the pregnant female are discriminated from movements of the fetus. More particularly, the analyzing device is adapted to perform all tasks of calculating and computing the measured data as well as determining and assessing results. This is achieved according to the invention by means of a computer software comprising computer instructions adapted for carrying out the steps of the inventive method, when the software is executed in a computer of the analyzing device. The analyzing device itself may comprise functional modules or units, which are implemented in form of hardware, software or in form of a combination of both.

The technical effects necessary according to the invention can thus be realized on the basis of the instructions of the computer program in accordance with the invention. Such a computer program can be stored on a carrier such as a CD-ROM or DVD or it can be available over the internet or another computer network. Prior to executing the computer program is loaded into the computer by reading the computer program from the carrier, for example by means of a CD-ROM or DVD player, or from the internet, and storing it in the memory of the computer. The computer includes inter alia a central processor unit (CPU), a bus system, memory means, e.g. RAM or ROM etc., storage means, e.g. floppy disk or hard disk units etc. and input/output units. Alternatively, the inventive method could be implemented in hardware, e.g. using one or more integrated circuits.

Figure 2:
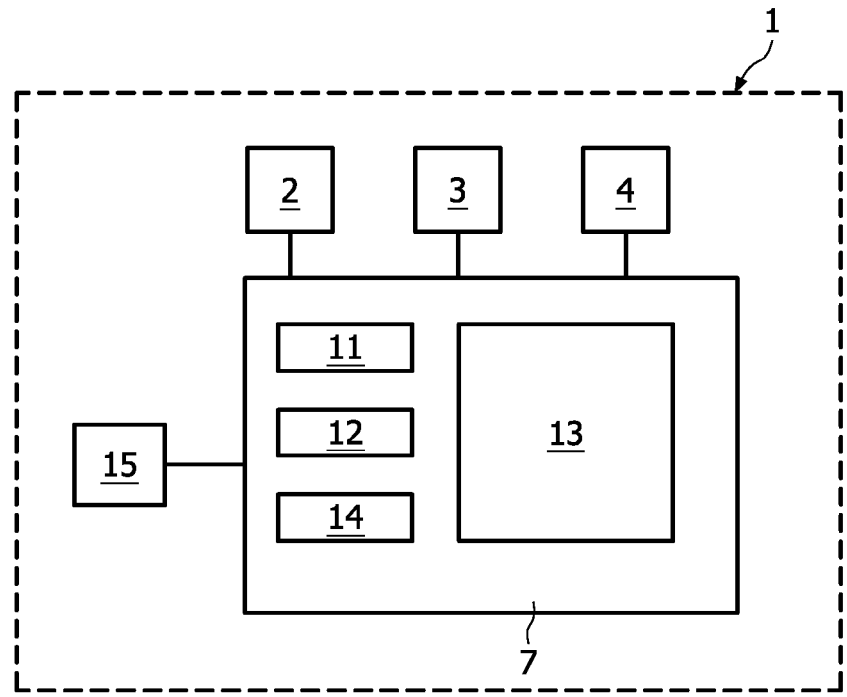
Figure 3:
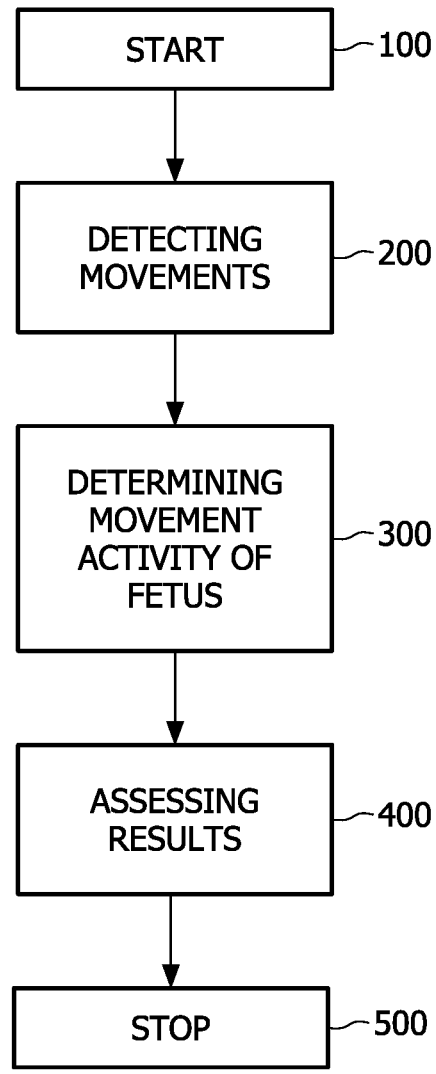
Figure 4:
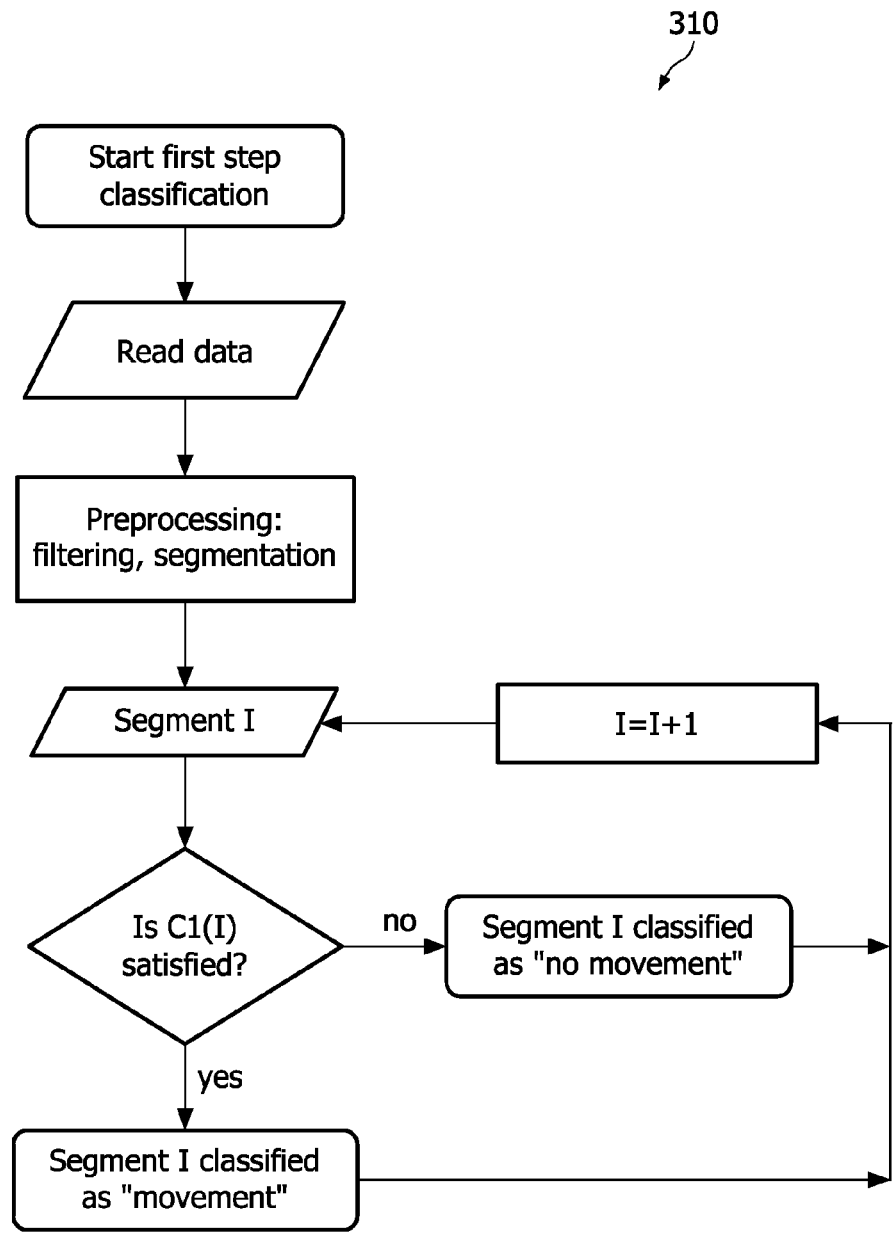
Figure 5:
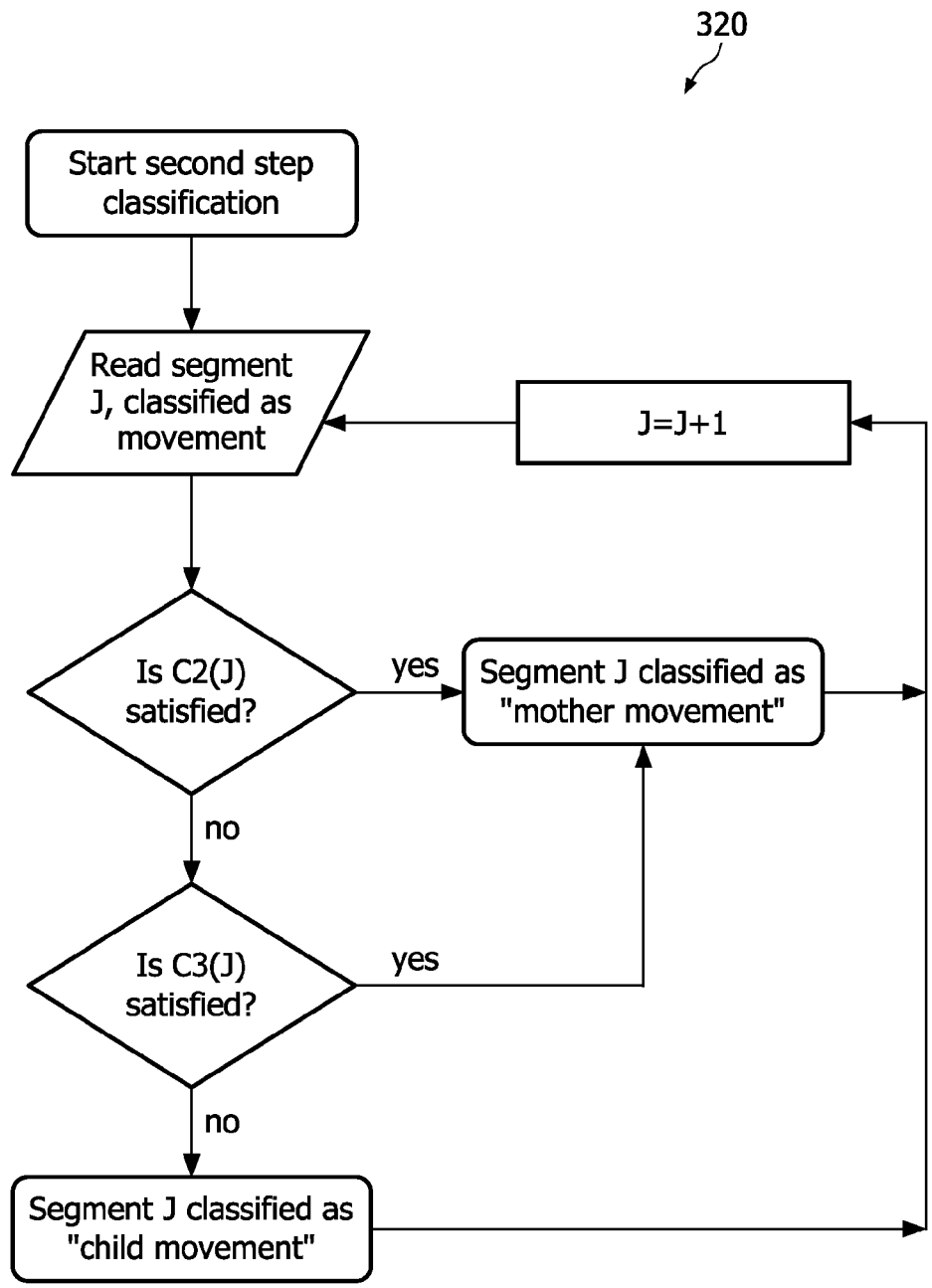
Figure 6:
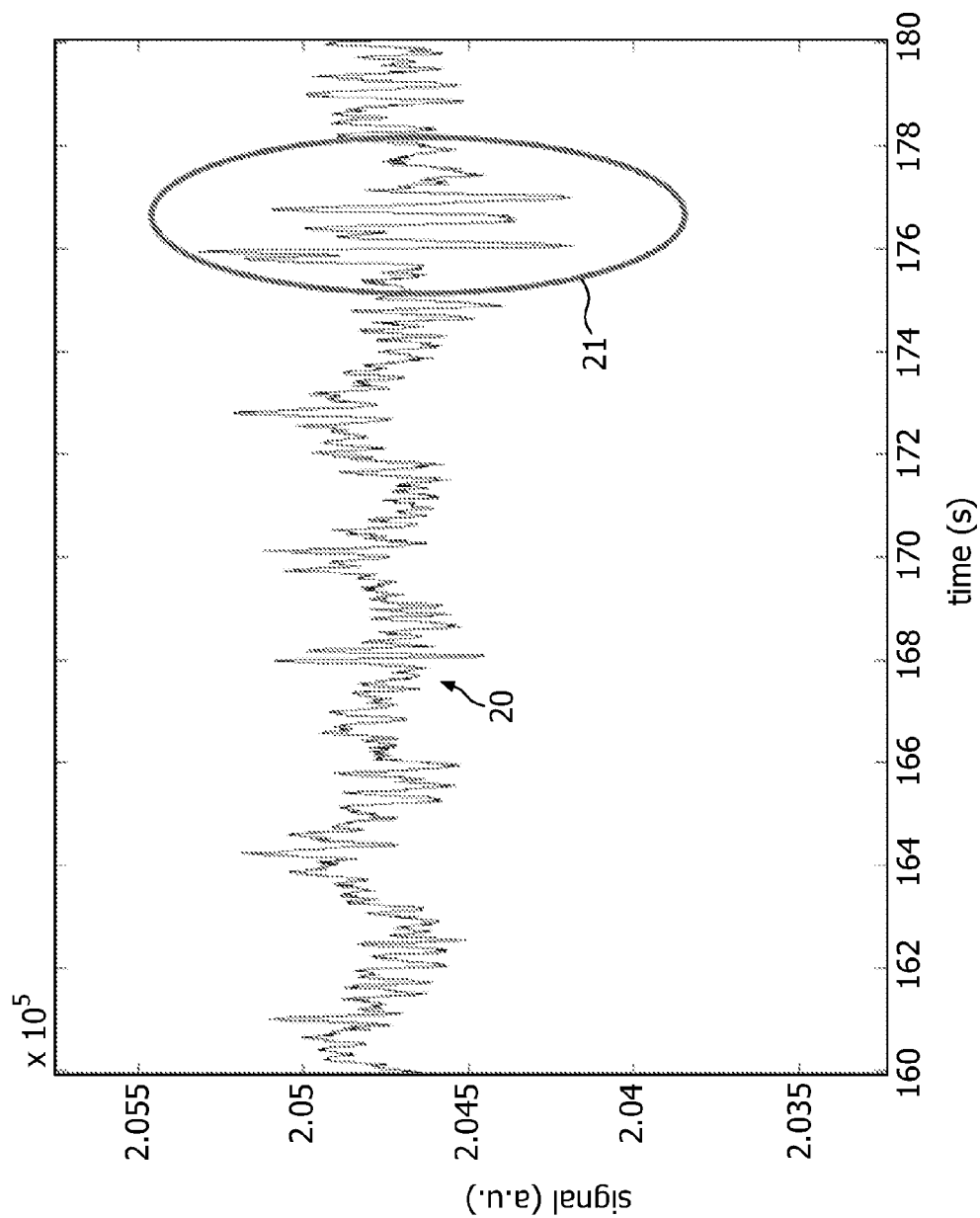
Figure 7:
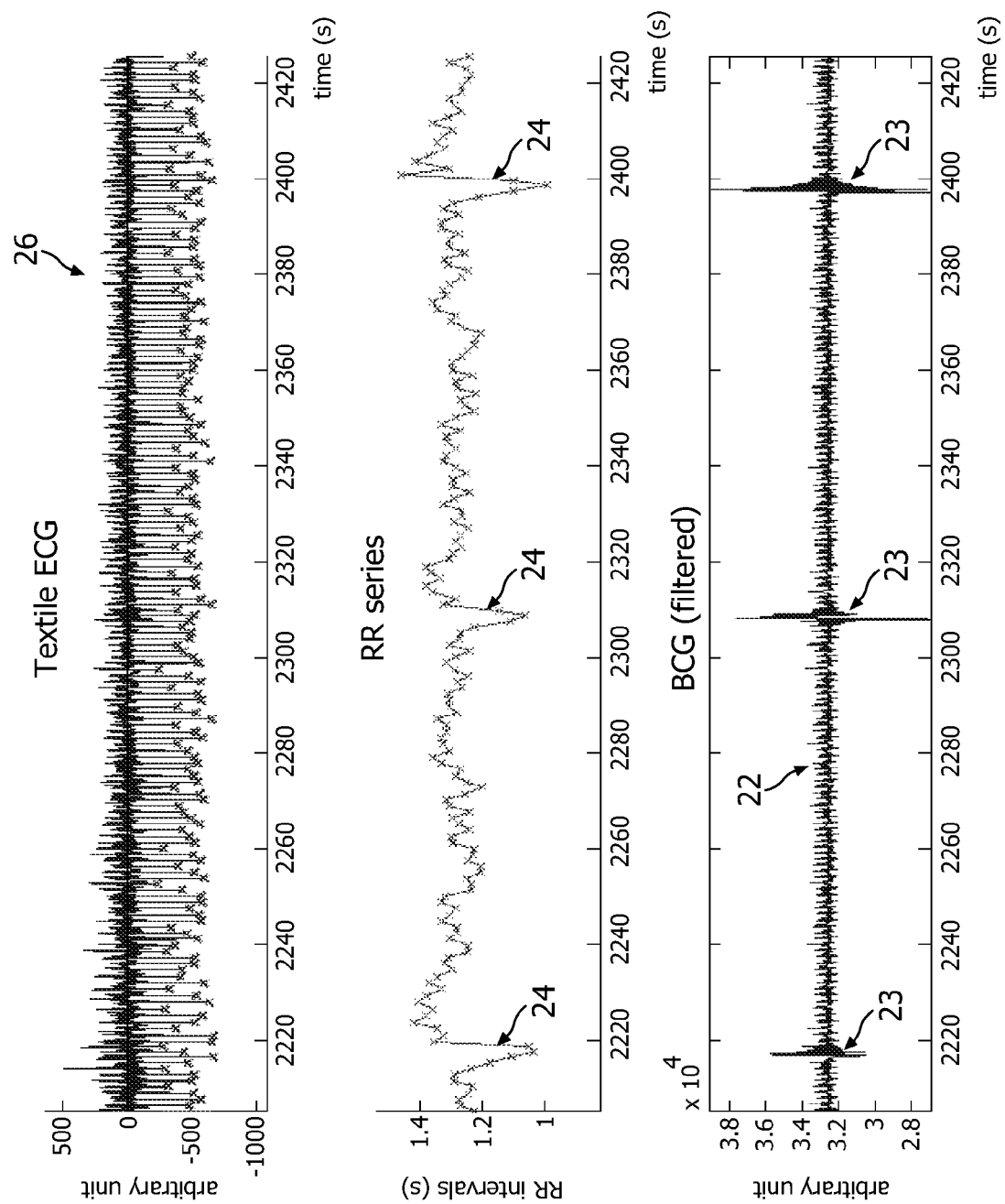
Figure 8:
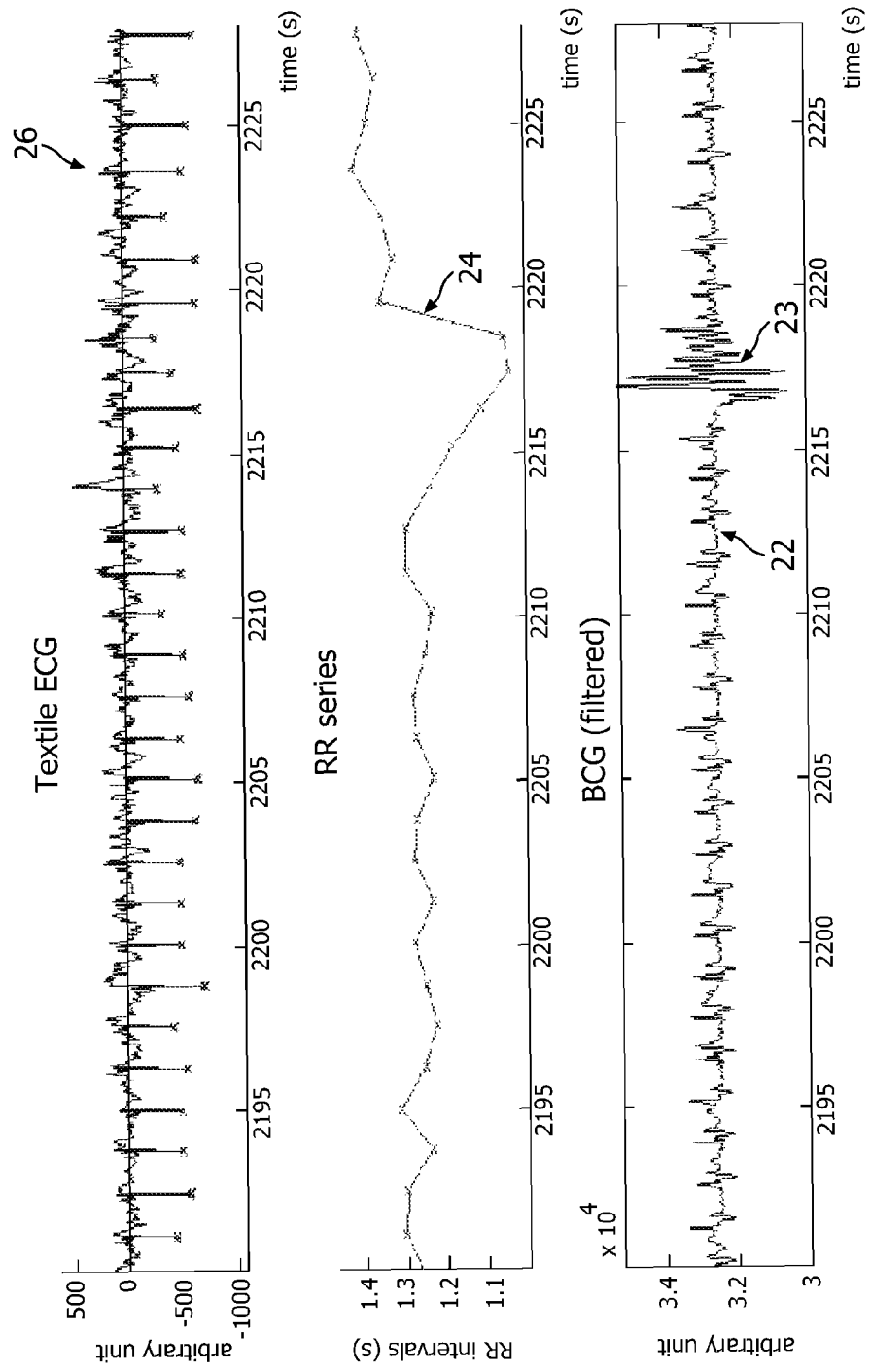
Figure 9:
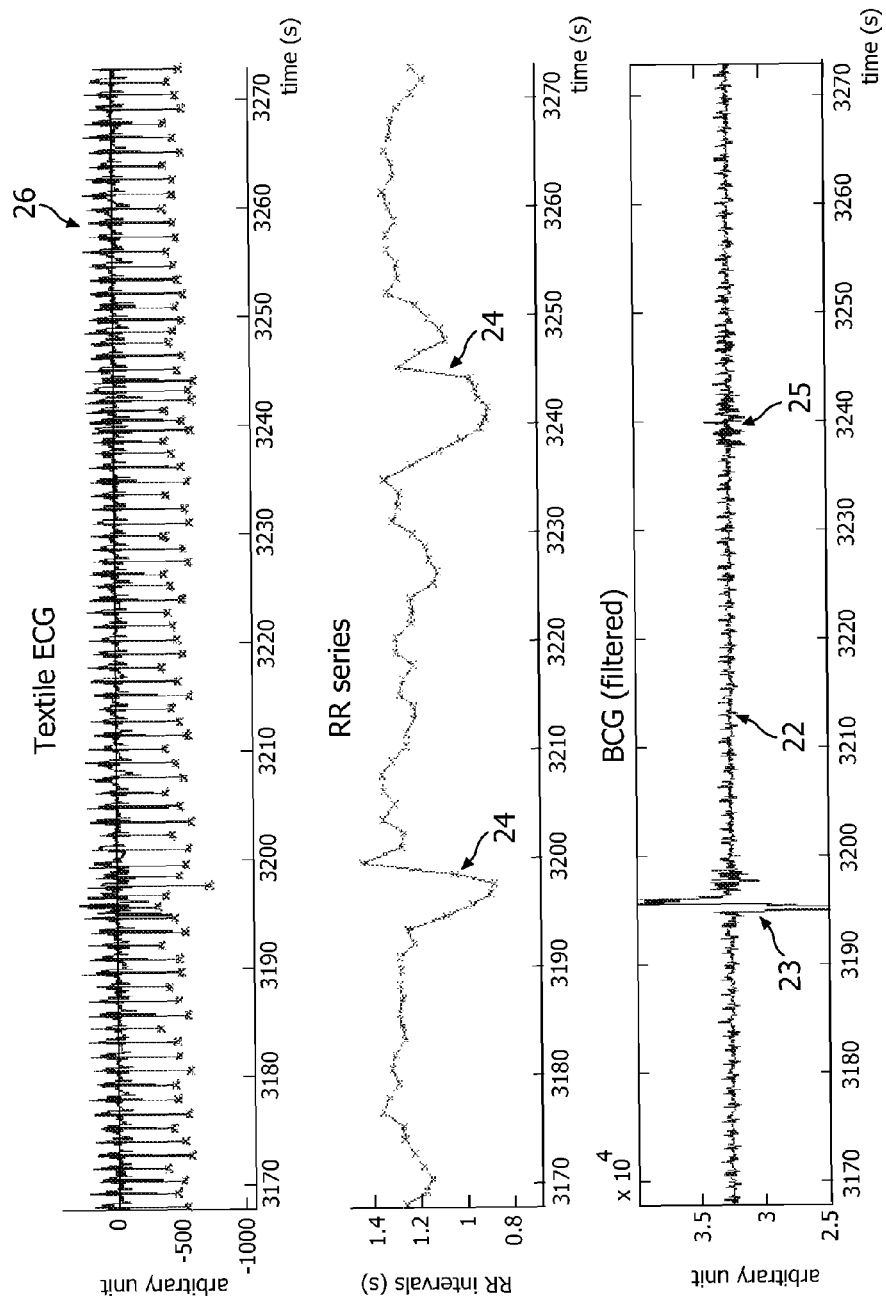
Figure 10:
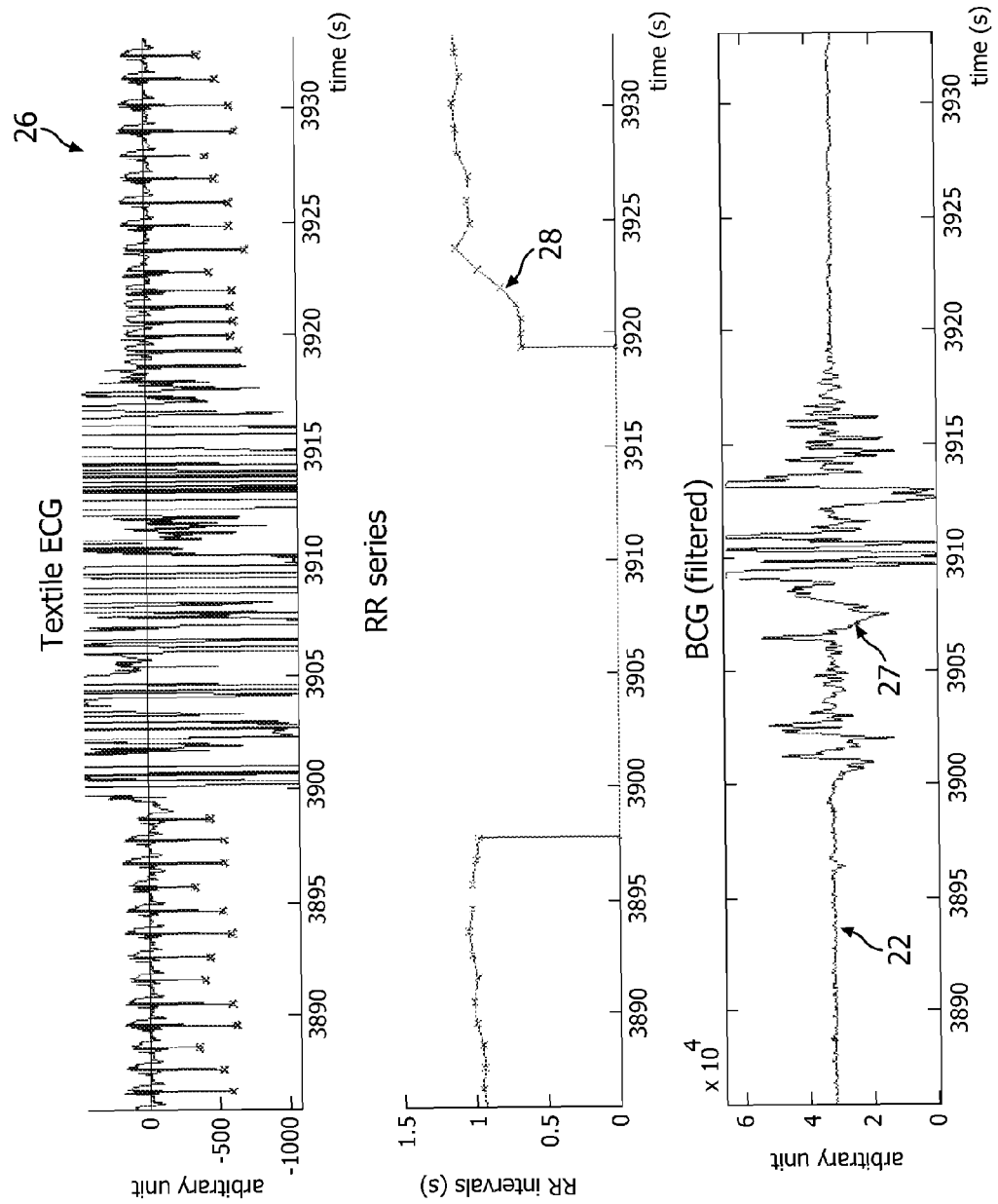

These and other aspects of the invention will be described in detail hereinafter, by way of example, with reference to the following embodiments and the accompanying drawings; in which:

FIG. 1 shows a bed with integrated sensors as used in a system according to the invention, FIG. 2 shows a schematic block diagram of a system according to the invention, FIG. 3 shows a simplified flowchart of the method according to the invention, FIG. 4 shows a more detailed flowchart of the method according to the invention, FIG. 5 shows a more detailed flowchart of the method according to the invention, FIG. 6 shows a BCG signal recorded for a pregnant woman with occurrence of a child movement, FIG. 7 shows ECG signal, RR series, and BCG signals recorded for a pregnant woman with three larger movements, FIG. 8 shows an enlarged portion of the signals from FIG. 7, FIG. 9 shows ECG signal, RR series, and BCG signals recorded for a pregnant woman with a very small movement, and FIG. 10 shows ECG signal, RR series, and BCG signals recorded for a pregnant woman with large signal disturbances.

With respect to FIGS. 1-5, the system and method according to the present invention is now explained in more detail. In general terms, the method comprises the steps of: starting 100 the measuring procedure; detecting 200 the overall movements of a pregnant woman, said overall movements comprising movements of the pregnant woman itself and movements of the unborn child; determining 300 the movement activity of the unborn child by analyzing the detected overall movements of the pregnant woman; assessing 400 results; and terminating 500 the measuring procedure. Preferably, the determining step 300 is carried out immediately after the movements occur. The determining step 300 may however be carried out at a later point in time.

For detecting the overall movements of a pregnant woman, the system 1 comprises a number of sensors 2. As sensors 2 piezoelectric sensors, electret foils or other suitable sensors, e.g. strain gauges, are used in order to obtain a ballistocardiogramm (BCG) of the pregnant woman. Additional sensors 3, e.g. textile electrocardiogram (ECG) sensors, are provided in order to measure the heart rate (HR) and heart rate variability (HRV) of the pregnant woman. The heart rate can however also be measured using the BCG sensors 2. Instead of the sensors listed above, other types of sensors may be used, depending on the type of measurement, the measuring environment and other requirements. All sensors 2, 3 are integrated into a conventional bed 5, in particular into a mattress 6 or the bedstead of the bed 7. The sensors 2, 3 are adapted and arranged in a way that allows all measurements (movement, ECG, BCG) to be performed if the pregnant woman is lying in the bed 5. Detailed information about a typical setup can be found in the patent applications WO2006111889 A1 and WO2006111878 A1, the disclosure of which is incorporated herein by reference.

The detecting step 200 not only comprises detecting movements by means of sensors 2, but also forwarding the movement signals to an analyzing device 7 of the system 1. The analyzing device 7 is adapted to determine the movement activity of the fetus by analyzing the detected overall movements of the pregnant female. The analyzing device 7 comprises a signal input module 11, an analogue-digital-converter 12 and a microprocessor 13. The signal input module 11, and the analogue-digital-converter 12 are used to deliver the incoming movement signals to the microprocessor 13. The microprocessor 13 is used for data processing and analyzing, as described in more detail below. In particular, all method steps carried out by the analyzing device 7 and described hereinafter are performed using a computer program executed in the microprocessor 13 of the analyzing device 7.

In the following, the process of discriminating movements of the pregnant female from movements of the fetus is explained. The discriminating is performed by means of the microprocessor 13, which serves as discriminator.

After the measured movement signal has been received by the analyzing device 7, subroutines 310, 320 of determining step 300 are carried out. A first step classification 310 is carried out by the analyzing device 7 in order to find segments I within the received signals, which can be classified as "movement", see FIG. 4. For this purpose the signal is divided into small segments with a length of e.g. 2 seconds. Then, a condition C1 is tested by means of the analyzing device 7 in order to assign each segment I in one of the two defined classes: "movement" or "no movement". Preferably, it is tested, whether the energy of the signal present in segment I under examination exceeds a first threshold value and whether the feature vector computed for this segment I has been assigned to the class "movement" or the class "no movement" by the classifier. The feature vector comprises e.g. several time domain features estimated from the signal, such as zero-crossing rate, first and second derivates. As a possible statistical pattern recognition approach, a Bayesian classifier with supervised training can be used to perform the segment classification. Other classifiers, e.g. artificial neural networks, with or without supervised training, as well as a structural pattern recognition approach can also be used.

Once a segment of data is classified as "movement", a second step classification 320 is carried out by the analyzing device 7. During this step the analyzing device 7 analyzes one by one those segments J, which have been classified as movements, in order to discriminate movements of the pregnant female from movements of the fetus. For this purpose the signal energy of the segment J under examination is analyzed and condition C2 is tested. If the signal energy exceeds a second threshold value, this particular movement will be assigned to a movement of the mother, and the next segment J is analyzed. The second threshold is higher than the first threshold.

If the energy of the detected movement signal does not exceed the second threshold value, this particular movement will be treated as related to a possible child movement, and the classification is continued. Subsequently, a condition C3 is tested. For this purpose it is determined by means of the analyzing device 7, whether the detected movement correlates with a changing heart rate HR of the mother. More particularly, it is determined, whether the heart rate increases in the time domain, and/or whether the heart rate variability HRV spectrum shows an increasing power in the low-frequency component. This test is based upon the insight, that the power of the low frequency component of the HRV spectrum is mediated by the sympathetic activity of the autonomous nervous system and increases in the presence of an increased sympathetic tone, which occurs during a motion. The presence of these changes are evaluated in segments J, . . . , K compared to previous segment(s), where K is the index of the first segment classified as "no movement". Preferably both conditions are tested in parallel. If at least one of these condition is fulfilled, the detected movement results from the mother. If the detected movement correlates with a changing heart rate HR of the mother, the movement is likely to be caused by the mother itself; and the next segment is analyzed. In cases, where a detected movement does not correlate with a changing of the mother's heart rate, this movement is likely to be caused by the fetus. Accordingly, the movement is classified as child movement.

Preferably, segment length, thresholds, etc. to be used during the determining step 300 are adaptively computed by means of the analyzing device 7. For example, the segment length is selected depending on the heart rate in order to obtain energy values within a defined range.

Using the determined child movements, the analyzing device 7 is further adapted to assess results in step 400, i.e. to provide a result information during the process of measuring and/or after the movement detecting is stopped. Preferably, the result comprises a simple pointer indicating the measurement outcome. Depending on the intended use, different types of pointer can be used. For example, a pointer which indicates the number of child movements can be provided; or the pointer indicates a presumable current status of the unborn child or a pointer, which indicates the movement history of child movements over the night. Preferably, in case the number of child movements falls below a certain threshold, the pointer indicates that the mother should ask for medical advice.

The analyzing device 7 further comprises a signal output module 14, which is adapted to deliver output signals and/or analyzing results (e.g. the pointer information) to a display 15 or the like, which is positioned near the bed. Alternatively the output module may be adapted to deliver output signals and/or analyzing results to an external receiver, which is situated e.g. at a local hospital or doctor. For this purpose a GSM network or a computer based network like the internet may be used.

The invention is now described with respect to measuring results as shown in FIGS. 6-10. A ballistocardiogramm (BCG) curve 20 of a (sleeping) pregnant woman is shown in FIG. 6. The BCG curve 20 is composed of two major frequency components: a low frequency sinusoidal component of high amplitude, related to the breathing movements of the pregnant woman, and a higher frequency component of small amplitude resulting from heart movements of the pregnant woman. In the specified circle 21 a typical signal for a child movement is shown (enlarged). It can clearly be discriminated from the resting signal.

Since movements of the child are generally of low energy, they are therefore characterized by small signal amplitudes. Hence, all movements with high amplitude can be attributed to the mother. Moreover, it has been observed that movements of the mother, including those with small amplitude, usually result in an increase in heart rate. This can be measured by recording an ECG in parallel, e.g. using textile or other ECG electrodes 3. The heart rate can also be determined by analyzing the BCG or using other sensors, like capacitive ECG sensors, which can measure the ECG without contact, inductive measuring sensors and radar based sensors.

In FIGS. 7-10, the sinusoidal breathing component is already removed from the BCG signal by filtering the measured BCG signals. The resulting BCG signal 22 is largely related to the heart rate of the pregnant woman. The filtering process is carried out during step 310 by the analyzing device 7, which comprises an appropriate filter means, e.g. as part of its signal processing unit realized by the microprocessor 13.

As illustrated in FIGS. 7-9, it is clearly visible that during sleep, small to very small movements 23 of the mother are correlated with an abrupt and punctual decrease 24 in the RR-intervals length, or equivalently an increase in the instantaneous heart rate. Motion is associated to a sympathetic activation, which could also be detected by a power increase in the low-frequency component of the HRV spectrum. Inversely, child movements do not have an effect on the heart rate or heart rate variability of the mother. After motion detection, it is therefore possible to discriminate between child and mother movements by analysis of the mother heart rate and heart rate variability spectrum.

Example of three movements 23 and their consequences over the instantaneous heart rate of the woman are given in FIG. 7. The RR series is derived from the simultaneously recorded textile ECG. Each movement 23 is correlated with an abrupt and punctual decrease 24 in the RR-intervals length. FIG. 8 shows an enlarged portion of the signals from FIG. 7.

FIG. 9 shows a first movement 23 at t=3196, which relates to a movement of the pregnant woman. Furthermore it shows an example of a very small movement 25 (second movement at t=3240). Now it has to be determined, whether this very small movement 25 results from the mother or the unborn child. Since the movement 25 is also associated with a decrease 24 in RR interval length, it results from the mother.

In the case where movements of the mother corrupt the ECG signal 26, it would still be possible by means of the analyzing device 7 to detect the sympathetic activation in the recovery phase 28 following the movement period 27, as illustrated in FIG. 10. Estimation of RR-intervals during motion (t=3900-3920) is not possible. However, the discriminating pattern in HR is nevertheless detectable directly after the movement in the recovery phase 28 (t=3919-3924).

It will be evident to those skilled in the art that the invention is not limited to the details of the foregoing illustrative embodiments, and that the present invention may be embodied in other specific forms without departing from the spirit or essential attributes thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein. It will furthermore be evident that the word "comprising" does not exclude other elements or steps, that the words "a" or "an" do not exclude a plurality, and that a single element, such as a computer system or another unit may fulfil the functions of several means recited in the claims. Any reference signs in the claims shall not be construed as limiting the claim concerned.

REFERENCE NUMERALS 1 system
2 BCG sensor
3 ECG sensor
4 (free)
5 bed
6 mattress
7 analyzing device
11 signal input device
12 A/D converter
13 microprocessor
14 signal output device
15 display
20 BCG signal
21 child movement
22 filtered BCG signal
23 movement
24 RR decrease
25 movement
26 ECG signal
27 movement period
28 recovery period
100-500 method steps

The invention claimed is:

1. A method of automatically monitoring movement activity of a fetus, the method comprising the steps of:
   detecting overall movements of a pregnant female, said overall movements comprising a combination of movements of the pregnant female and movements of the fetus;
   detecting at least one second physiological signal of the pregnant female; and
   determining the movement activity of the fetus by analyzing the detected overall movements of the pregnant female, analyzing the at least one second physiological signal of the pregnant female, and discriminating movements of the pregnant female from independent movements of the fetus depending on the analyzing results.

2. The method as claimed in claim 1, wherein the energy of a movement signal of the pregnant female is analyzed.

3. The method as claimed in claim 1, wherein the pregnant female's heart rate and/or heart rate variability is used as second physiological signal.

4. The method as claimed in claim 3, wherein a movement is classified as child movement, if the movement does not correlate with a changing of the pregnant female's heart rate.

5. The method as claimed in claim 1, wherein the movements of the pregnant female are detected during the pregnant female's sleep.

6. A system for automatically monitoring movement activity of a fetus, the system comprising:
   at least one sensor for detecting overall movements of a pregnant female, said overall movements comprising a combination of movements of the pregnant female and movements of the fetus;
   at least one sensor for detecting at least one second physiological signal of the pregnant female; and
   an analyzing device for determining the movement activity of the fetus by analyzing the detected overall movements of the pregnant female and analyzing the at least one second physiological signal of the pregnant female; said analyzing device comprising a discriminator for discriminating movements of the pregnant female from independent movements of the fetus depending on the analyzing results.

7. The system as claimed in claim 6, wherein the at least one sensor for detecting movements and/or the at least one sensor for detecting at least one second physiological signal of the pregnant female is connected to or integrated into a bed.

8. A computer program embodied on a memory and executed by a processor of a computer, for automatically monitoring movement activity of a fetus, said computer program comprising computer instructions to determine the movement activity of a fetus by:
   analyzing previously detected overall movements of a pregnant female, said overall movements comprising a combination of movements of the pregnant female and movements of the fetus;
   analyzing at least one previously detected second physiological signal of the pregnant female; and
   discriminating movements of the pregnant female from independent movements of the fetus depending on the analyzing results.

* * * * *